United States Patent
Budnik et al.

[11] Patent Number: 5,868,731
[45] Date of Patent: Feb. 9, 1999

[54] LASER SURGICAL DEVICE AND METHOD OF ITS USE

[75] Inventors: Vladimir N. Budnik; Valentin A. Gruzdev; Oleg D. Odintsov, all of Moscow, Russian Federation

[73] Assignee: Innotech USA, Inc., Ardsley, N.Y.

[21] Appl. No.: 610,211

[22] Filed: Mar. 4, 1996

[51] Int. Cl.⁶ ............................................ A61N 5/06
[52] U.S. Cl. ........................... 606/9; 606/13; 607/89
[58] Field of Search ................. 606/2, 3, 9, 10, 606/11, 12, 13; 607/88, 89, 90, 91; 372/34, 109, 35

[56] References Cited

U.S. PATENT DOCUMENTS

| | | |
|---|---|---|
| 3,487,835 | 1/1970 | Koester et al. . |
| 3,516,011 | 6/1970 | Hadwin ............................. 372/34 |
| 4,316,467 | 2/1982 | Muckerheide . |
| 4,388,924 | 6/1983 | Weissman et al. . |
| 4,408,602 | 10/1983 | Nakajima . |
| 4,478,217 | 10/1984 | Shimada et al. . |
| 4,564,011 | 1/1986 | Goldman . |
| 4,608,978 | 9/1986 | Rohr . |
| 4,653,495 | 3/1987 | Nanaumi . |
| 4,674,497 | 6/1987 | Ogasawara . |
| 4,733,660 | 3/1988 | Itzkan . |
| 4,737,628 | 4/1988 | Lovo . |
| 4,791,927 | 12/1988 | Menger . |
| 4,836,203 | 6/1989 | Müller et al. . |
| 4,854,320 | 8/1989 | Dew et al. . |
| 4,950,266 | 8/1990 | Sinofsky ........................... 606/2 |
| 5,005,180 | 4/1991 | Edelman et al. . |
| 5,057,104 | 10/1991 | Chess . |
| 5,066,293 | 11/1991 | Furumoto . |
| 5,074,861 | 12/1991 | Schneider et al. .................. 606/3 |
| 5,125,922 | 6/1992 | Dwyer et al. . |
| 5,165,418 | 11/1992 | Tankovich . |
| 5,182,857 | 2/1993 | Simon . |
| 5,192,278 | 3/1993 | Hayes et al. ...................... 606/7 |
| 5,207,670 | 5/1993 | Sinofsky . |
| 5,281,211 | 1/1994 | Parel et al. . |
| 5,318,562 | 6/1994 | Levy et al. . |
| 5,334,191 | 8/1994 | Poppas et al. . |
| 5,344,418 | 9/1994 | Ghaffari . |
| 5,348,552 | 9/1994 | Nakajima et al. . |
| 5,364,390 | 11/1994 | Taboada et al. . |
| 5,401,171 | 3/1995 | Paghdiwala . |
| 5,409,481 | 4/1995 | Poppas et al. . |
| 5,456,603 | 10/1995 | Kowalyk et al. . |
| 5,481,556 | 1/1996 | Daikuzono ........................ 372/34 |
| 5,628,744 | 5/1997 | Coleman et al. ................. 606/10 |

Primary Examiner—John P. Lacyk
Assistant Examiner—Eric F. Winakur
Attorney, Agent, or Firm—Lawrence G. Fridman

[57] ABSTRACT

A laser surgical device for vaporization of a living tissue consists of an operating laser assembly, a detecting arrangement and a control unit. The operating laser assembly generates an operating beam having a predetermined wavelength corresponding to a peak absorption wavelength of water. The detecting arrangement is adopted for detecting a condition of an operated living tissue by receiving and reviewing a signal reflected from the operated living tissue so as to produce a control signal. The control unit controls characteristics of the operating beam based on the control signal, so that the depth of vaporization of the living tissue does not exceed 15–20 microns.

22 Claims, 6 Drawing Sheets

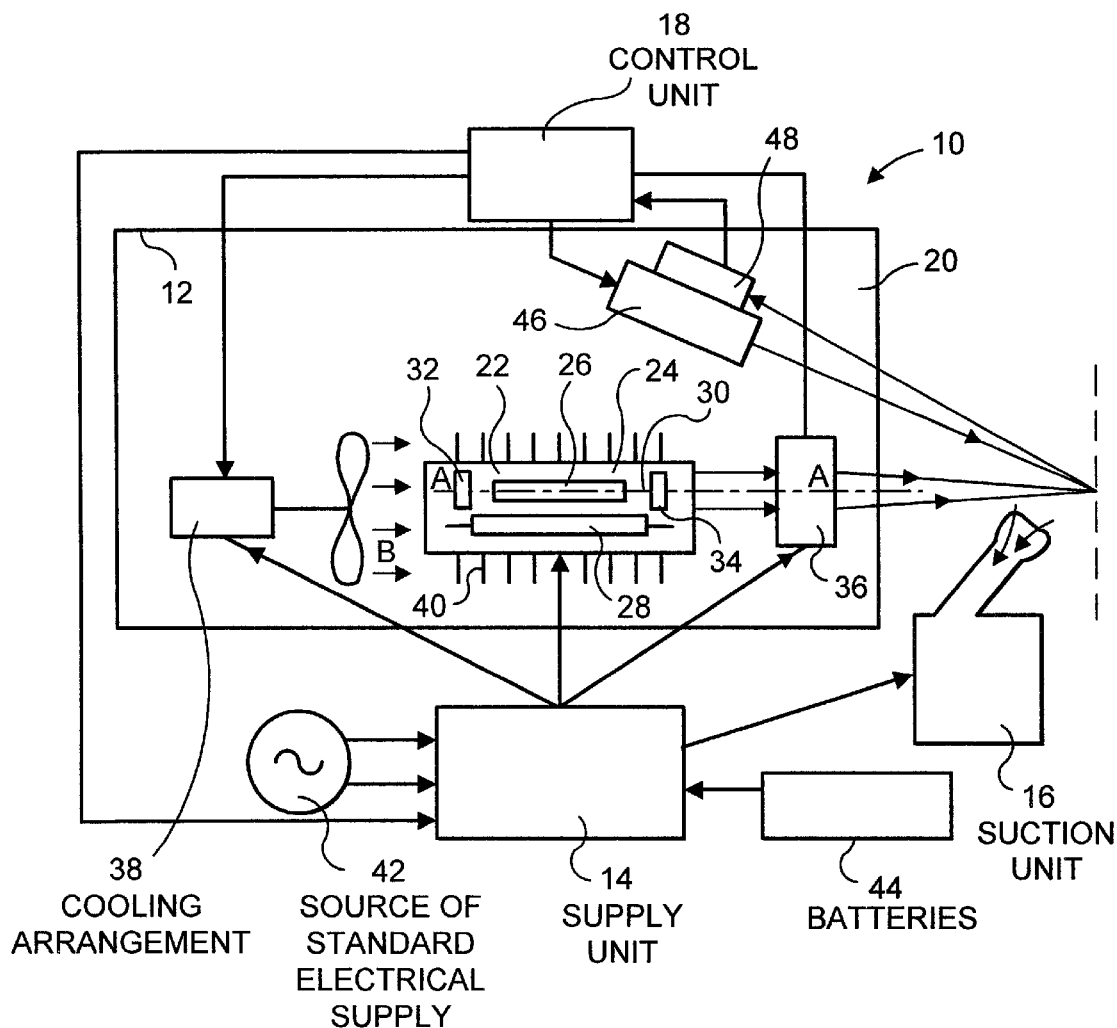
F I G. 2

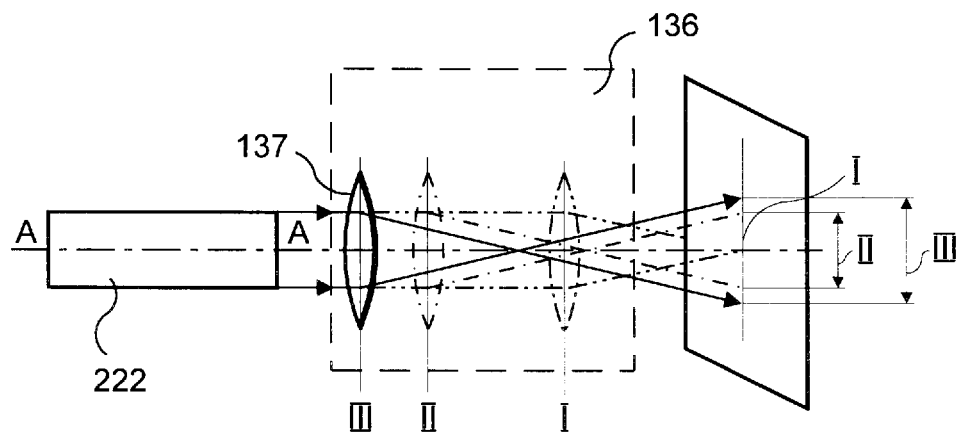
F I G. 7
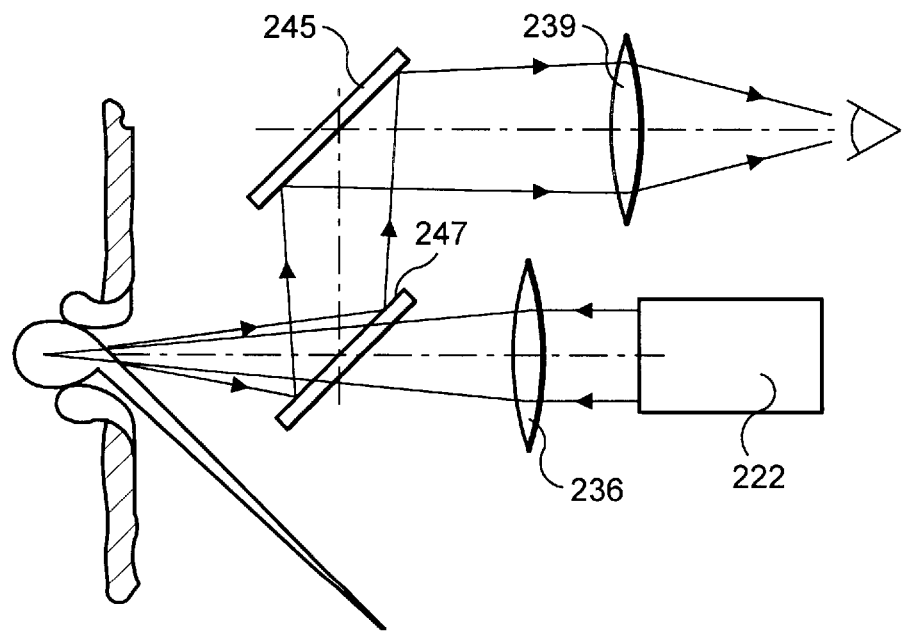
F I G. 10

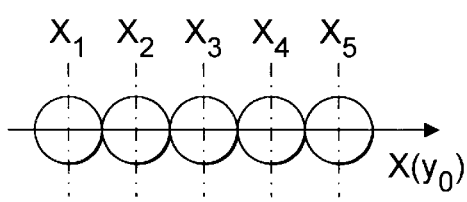
F I G. 11
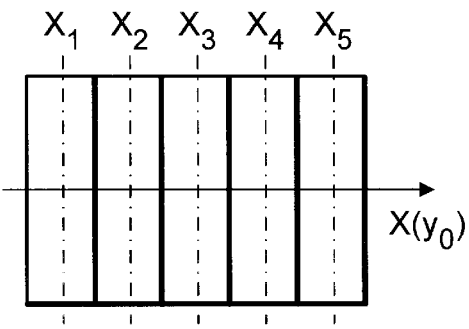
F I G. 12
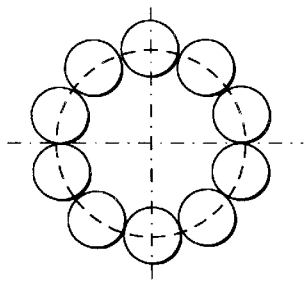
F I G. 13
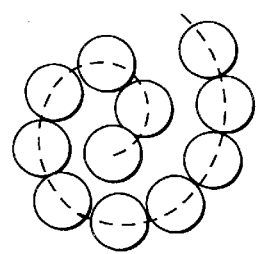
F I G. 14
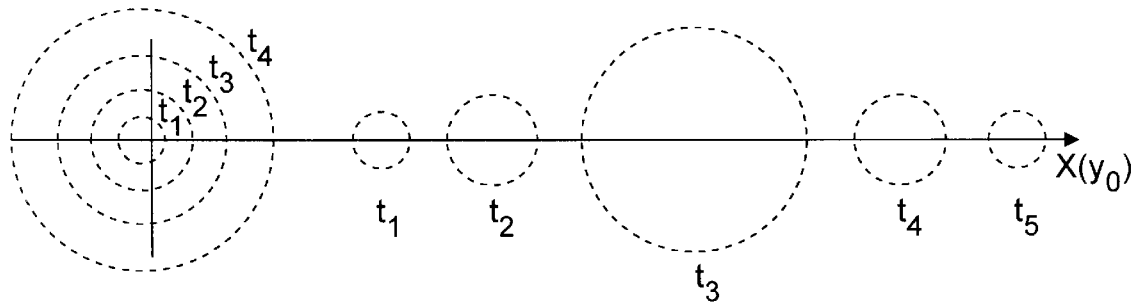
F I G. 15
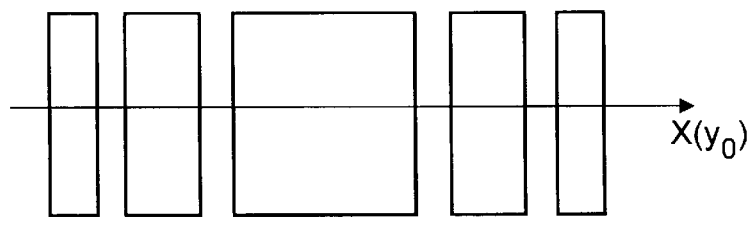
F I G. 16

LASER SURGICAL DEVICE AND METHOD OF ITS USE

FIELD OF THE INVENTION

This invention relates to medical lasers, and more particularly to a surgical laser device and a method of its use in the field of dermatology.

BACKGROUND OF THE INVENTION.

A variety of lasers have been used in modern dermatology for correction of inborn and acquired skin defects and diseases. One of the reasons for wide proliferation of the lasers in this field is that their properties are well support the principle postulate of medicine—"do not harm" a patient.

Drug therapy has been the most commonly used method of treatment in dermatology mainly because it is readily available, simple and less painful. However, drug intolerance, side effects, common allergic reactions as well as low efficiency in treatment of a substantial number of disorders often make this treatment less desirable.

A need for more efficient cure of dermatological defects and diseases made surgical involvement quite popular in this area of medicine. As to the surgical methods of treatment of skin disorders, doctors are often compelled to resort to such procedures as: dissection followed by transplantation, use of ultrasound and cryotherapy, application of magnetic fields of ionizing radiation, electrocoagulation, utilizing of plasma currents, etc. These surgical methods are used in spite of a great number of drawbacks and harmful side effects which include: destructive nature of the treatment, protractive healing process, high risk of hypopigmentation, possibility of atrophy, destruction of a skin texture, formation of scars, damage to an adjacent skin area including healthy regions. These problems are often alleviated when a surgeon uses local methods of treatment having short and fixed duration of action at a specified depth of a skin integument. This is one of the reasons why lasers have become recently the instrument of choice of many dermatologists.

Currently, lasers having different wavelength of laser irradiation are used in dermatology. Examples of such lasers are: excimer, ruby, argon laser; alexandrite and garnet laser; tunable semiconductor laser; etc. These devices generate laser beams having the wavelength in the visible range of the spectrum (0.4–0.7 $\mu$m) as well as in the invisible, the UV range (0.18–0.40 $\mu$m). For instance, infrared lasers include a set of $CO_2$ lasers (with the wavelength of 10.6 $\mu$m), variations of neodymium lasers (with the wavelength of 1.06 $\mu$m), etc. These lasers are produced by Candela Laser Corporation and are described by "Lasers in Medicine" Tashkent, 1989.

In spite of the fact that these lasers maintain a short duration of action and provide certain localization in the plane of the action, they do not guarantee control of the treatment, especially as to the depth of penetration in the skin integument. Thus, use of these lasers does not eliminate such negative consequences as formation of hypotrophical scars and penetration of a laser beam into the area of healthy skin.

It is a matter of general knowledge that a layer of water practically does not allow optical irradiation at certain wavelength to pass therethrough. This region of the spectrum is typically known as the window of non-transparency and includes the following wavelength ranges: 1.25–1.40; 1.7–2.1; 2.5–3.1 and 5.5–7.5 microns. At these ranges optical irradiation is strongly absorbed by water and by living tissue which consists up to 90 percent water. Such absorption leads to a rapid heating of water and vaporization of the treated living tissue. At these wavelengths a laser beam acquires an important quality, that is that laser irradiation cannot penetrate deeply into living tissue substantially consisting of water. As a result, a scattered laser beam propagates in living tissue only within the range which does not exceed the depth of 15–20 microns and does not destroy adjacent tissue. Such a mode of operation of a laser can be implemented only at specific levels of power density and energy, predetermined rate and duration of the pulse and only when a temporary stability of all these characteristics is achieved during a surgical procedure.

One of such known devices is the aluminum-yttrium-erbium garnet laser having the wavelength of 2.94 $\mu$m of laser irradiation. Initial reports about stomatological application of this laser appeared in 1989. However, its properties such as energy pulse of 1–2 J; the wavelength of 2.94 $\mu$m and the pulse rate of 1 Hz enabled doctors to use this laser as surgical device in the field of dermatology. The first reports of such use became known in Germany and Slovenia in 1991.

A schematic diagram of FIG. 1 illustrates that such device consists of a power unit, a cooling unit, a laser cavity and an articulated mirror guide light unit. In view of the multiple reflection of the laser beam in the articulated mirror guide light unit the efficiency of the device is quite low and does not exceed 60 percents at the wavelength of 2.94 $\mu$m. This makes it necessary to sustain energy input of the laser irradiation at the level 2.5–3.0 J and the operating power of the power unit at 300 W. Naturally, a laser of such high power has to have a very efficient cooling system. Therefore, a special water cooling system was provided in this prior art device. In view of that, the weight of the device was 70 kgs with overall dimensions of 0.5 $m^3$. Thus, large weight and dimensions as well as instability of the laser beam characteristics greatly limited employment of this prior art laser in dermatology.

The water cooling system was necessary in the high powered prior art device to keep the temperature of the active element within 20±10° C. range. When this temperature range was exceeded the thermolens effect developed in the active element which resulted in considerable laser beam scattering and in the loss of energy in the focal plane of a treated tissue.

One way of resolving these problems is through the formation of more efficient laser system which lacks of the articulated mirror guide light and requires substantially less power. This makes possible the replacement of the water cooling system by its air cooling counterpart. Such changes ultimately lead to a substantial reduction of the weight and overall dimensions of the laser assembly.

Thus, there has been a considerable need for an efficient hand held laser surgical device usable in the field of dermatology which is capable of providing and controlling a predetermined depth of skin penetration and does not damage healthy regions of tissue adjacent the operation site.

SUMMARY OF THE INVENTION

One aspect of the present invention provides a laser surgical device for vaporization of a living tissue. The device consists of an operating laser assembly, a detecting arrangement and a control unit. The operating laser assembly generates an operating beam having a predetermined wavelength corresponding to a peak absorption wavelength of water. The detecting arrangement is provided for detecting conditions of an operated living tissue by receiving and reviewing a radiation signal reflected from the operated living tissue and producing a control signal. The control unit controls and adjusts characteristics of the operating beam based on the control signal, so that the depth of vaporization of the living tissue does not exceed 15–20 microns. The device also includes a power unit, a focusing arrangement for focusing the operating beam at the operated living tissue, a guide light unit generating a guide light beam for targeting the operating beam at the operated living tissue and a cooling unit for cooling of at least a portion of the operating laser assembly. The suction arrangement is provided for removal of disintegrated tissue products from the area of the operated living tissue.

A further aspect of the invention provides the operating laser assembly consisting of at least an operating laser element emitting the operating beam and exciting arrangement for its exciting. A handpiece is adopted for convenient positioning in the hands of an operator. The handpiece has interior and exterior parts and at least a portion of the operating laser assembly and focusing arrangement are situated within the interior part of the handpiece. At least portions of the cooling unit, the detecting arrangement and the control unit are also situated within the interior portion of the handpiece.

Another aspect of the invention provides a device in which at least a portion of the operating laser assembly is positioned within the housing and the cooling unit is a fan producing an air flow extending longitudinally within the interior portion of the handpiece.

Still another aspect of the invention provides the device in which the exciting arrangement is positioned outside the handpiece and is connected to the operating laser assembly by a plurality of optical fibers.

Still further aspect of the invention provides a device with the operating laser element consisting of working and auxiliary portions. The working portion is situated in the handpiece, whereas the auxiliary portion and the exciting arrangement are situated outside the handpiece. The main and auxiliary portions of the operating laser element are connected through a light guide consisting of a plurality of optical fibers.

Yet another aspect of the invention provides the device in which the wavelength of the operating beam emitted by the operating laser element is selected from the group consisting of 1.25–1.40, 1.7–2.1; 2.5–3.1 and 5.5–7.5 microns. The laser medium of the operating laser element is selected from the group consisting essentially $Y_3AL_5O_{12}$:Nd; $Gd_3Ga_5O_{12}$:Cr, Ce, Nd; $MgF_2$:Co; $BaYb_2F_8$:Er; $LiYF_4$:Er:Tm, Ho; $Y_3Sc_2Al_3O_{12}$:Cr,Er; $(Y,Er)_3Al_5O_{12}$; HF (chemical) and CO (gaseous).

Alternatively, the method of surgical vaporization of a living tissue can be provided. The method comprises the steps of generating an operating laser beam having a predetermined wavelength corresponding to a peak absorption wavelength of water and detecting a condition of operating living tissue by receiving and reviewing a radiation signal reflected from the tissue and producing a control signal. A further step of the method is controlling and adjusting characteristics of the operating beam based on the control signal, so that the depth of the vaporization of the living tissue does not exceed 15–20 microns.

BRIEF DESCRIPTION OF THE DRAWINGS

Other advantages and features of the invention are described with reference to exemplary embodiments, which are intended to explain and not to limit the invention, and are illustrated in the drawings in which:

FIG. 2 shows one embodiment of a laser surgical device of the invention;

FIG. 7 illustrates alternative positions of the lens of focusing arrangement;

FIG. 10 shows application of an accessory lens to the laser surgical device;

FIGS. 11 and 12 illustrate different patterns of laser beam images;

FIGS. 13 and 14 illustrate further patterns of laser beam images;

FIG. 15 illustrates conditions of beam scanning at a preset program; and

FIG. 16 illustrates conditions of beam scanning when the laser beam is in the slot form.

DETAILED DESCRIPTION OF THE PREFERRED EMBODIMENT

Figure 1:
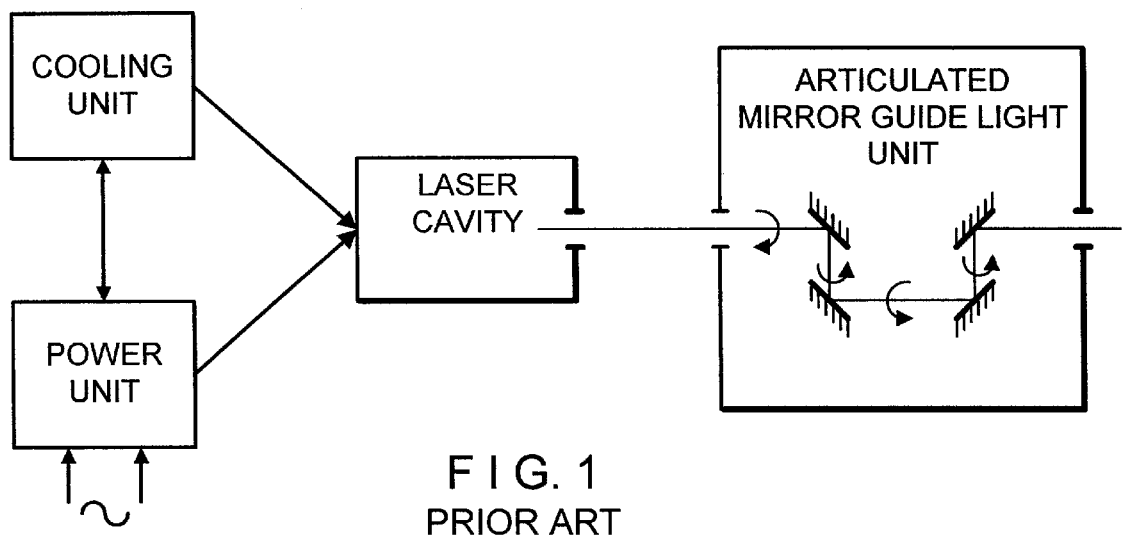
FIG. 1 shows a prior art laser device.

Although specific embodiments of the invention will now be described with reference to the drawings, it should be understood that the embodiments shown are by way of examples only and merely illustrative of but few of many possible specific embodiments which represent application of the principles of the invention. Various changes and modifications obvious to one skilled in the art to which the invention pertains are deemed to be within the spirit, scope and contemplation of the invention as further defined in the appended claims.

It was indicated hereinabove that the optical irradiation in the wavelength region corresponding to the "windows of non-transparency" is very efficiently absorbed by water and living tissue. The operating beam of the laser surgical device of the present invention efficiently performs within such entire wavelength region. As a result of application of the laser beam to the targeted area of a patient, a local vaporization of the top skin layer occurs at the maximum depth of 10–20 microns. The diameter of the irradiated spot on the skin is about 10 mm and the density is in the range of 5–50 $J/cm^2$.

Referring now to the drawings, in which there is shown in FIG. 2 an apparatus 10 for performing of a laser surgery. The apparatus 10 consists of the following main units: a compact surgical laser instrument or a handpiece 12, a power supply unit 14 producing high-voltage potential pulses with tunable parameters, a suction unit or suction apparatus 16 for suction of disintegrated skin products resulted from application of an operating laser beam to a targeted area and a control unit 18. The handpiece formed with a housing 20 is adopted to be conveniently held in the hands of an operator. It is best illustrated in FIG. 2 that a laser cavity 22 is provided within the interior area of the housing 20. In operating laser assembly 24 is situated within the laser cavity and consists of an active laser element or rod 26, an exciting arrangement 28 and an optical resonator 30. The exciting arrangement which is adopted for exciting of the operating laser element can be any conventional exciting device such as, for example, a flash lamp or a diode laser.

The optical resonator 30 includes a mirror 32 having high reflective capabilities and positioned rearwardly of the laser element and a semi-reflective operating mirror 34 situated forwardly of the laser element so as to face a variable focusing lens 36. The mirrors of the optical resonator are disposed in the coaxial manner to a longitudinal axis A—A of the laser rod 26 and operating laser beam. The focusing lens 36 which is at least partially positioned within the housing 20 is typically operated by a micromotor on command from the control unit 18. A desired position of the focusing lens 36 can be also arranged manually by a medical personnel before or during a surgery. The optical resonator 30 is adopted to align and amplify the laser beam, whereas the focusing lens 36 directs it to the targeted area. In order to facilitate efficient delivery of the light energy from the exciting arrangement 28 to the operating laser element 26, the interior of the laser cavity can be covered by a material of high reflectivity.

A cooling arrangement 38 is provided within the housing 20 rearwardly of the laser cavity 22. The cooling arrangement can be of any known type producing an axial stream of gaseous coolant. In the preferred embodiment of the invention the cooling arrangement is a fan 38 which generates an axially directed air stream B extending longitudinally in the interior of the housing 20. In order to increase efficiency of the cooling process the exterior of the laser cavity 22 is formed with a plurality of ribs 40 extending outwardly therefrom. Thus, upon activation of the fan, axially directed air stream B is blown over the exterior of the laser cavity 22, including the ribs 40 reducing their temperature. The air stream B during its travel within the handpiece is directed through openings in the housing (not shown) to the exterior parts of the focusing lens 36, so as to prevent pollution of the lens by disintegrated skin products resulted from the surgery. Upon reaching the operated area of the skin, the air stream B also facilitates removal of the disintegrated tissue products from the site of the surgery and reduces effect of an unpleasant odor on a medical personnel.

Longitudinal distribution of the elements of the invention within the housing 20 helps to reduce the dimensions and facilitates efficient delivery of the air coolant and reduction of temperature of the laser cavity and throughout the interior area of the handpiece. Furthermore, use of air cooling system results in better stability of temperature and other characteristics of the laser cavity, especially during and after multiple thermocycling.

The surgical apparatus 10 is energized through a source of standard electrical supply 42 or through a set of batteries 44. In order to eliminate any potential shock hazard specially upon switching the power from the source of standard electrical supply to the battery unit, a power interlock switch can be provided.

The power supply unit 14 generates electrical voltage pulses which are converted by the exciting arrangement or the flash lamp 28 into light pulses. In the laser cavity 22, after being directed to the laser rod 26, such light pulses are converted into laser pulses having shorter duration of emission compared to the voltage pulses. The wavelength of the laser irradiation is determined by the type of the laser rod or active element utilized by the surgical apparatus. In the preferred embodiment of the invention Er:YAG (erbium) laser is used as the active element or laser rod 26 of the surgical apparatus. The laser rod made of this material emits the electromagnetic energy corresponding to the wavelength of the "windows of non-transparency" of water. The wavelength of this laser is 2.94 $\mu$m and is very close to the maximum absorption wavelength of water, which is about 3 $\mu$m. Thus, at this wavelength of the operating laser beam a great portion of its energy is absorbed by the operated living tissue which up to 90 percents consists of water.

The essential requirement for the materials used in the active element of the operating laser is that the wavelength of their irradiation belong to the "windows of non-transparency" region of the spectrum. Therefore, the laser medium of the active element of the invention can be selected from, but is not limited to, the following group of materials which forms a part of this category: $Y_3AL_5O_{12}$:Nd (wavelength 1.33 $\mu$m); $Gd_3Ga_5O_{12}$:Cr, Ce, Nd (wavelength 1.42 $\mu$m); $MgF_2$:Co (wavelength 1.75 $\mu$m); $BaYb_2F_8$:Er (wavelength 2.0 $\mu$m); $LiYF_4$:Er,Tm,Ho (wavelength 2.06 $\mu$m); $Y_3SC_2Al_3O_{12}$:Cr,Er (wavelength 2.8 $\mu$m); (Y,Er)$_3Al_5O_{12}$ (wavelength 2.94 $\mu$m); HF—chemical (wavelength 2.6–3.0 $\mu$m) and CO-gaseous (wavelength 5.0–6.0 $\mu$m).

Figure 3:
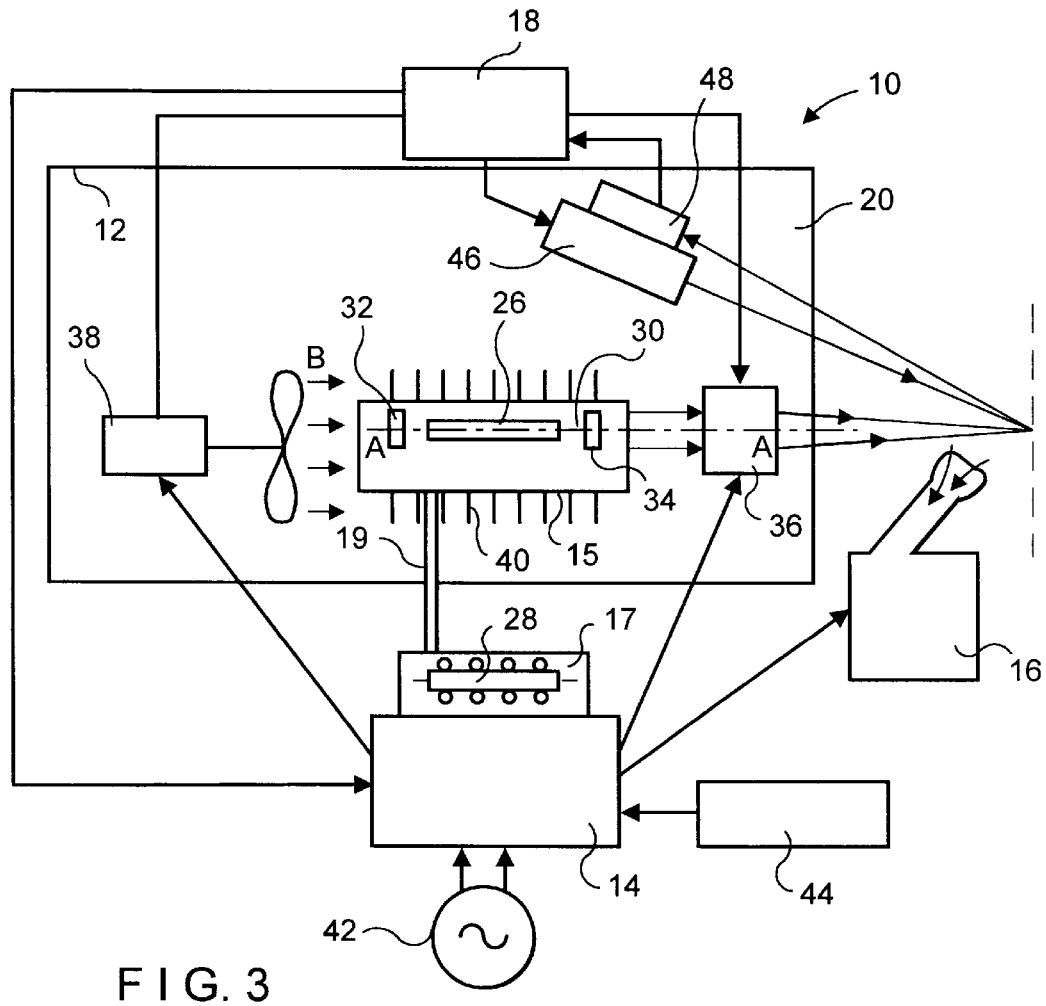
FIG. 3 shows another embodiment of the laser surgical device.

This wavelength of the operating laser beam belongs to the infrared region of the spectrum and is invisible to the naked eyes of a surgical operator. In view of that, an operator can not observe the emission of the operating laser beam from the forefront of the handpiece. This might cause erroneous surgical steps raising serious questions of security in the medical treatment. To eliminate this drawback, in the invention a guide light unit 46 generating a continuous, visible guide light beam is provided. Such guide light unit can be He:Ne laser, semiconductor laser, light-emitting diodes or any other suitable source of visible radiation. In the embodiment of the invention illustrated in FIG. 2 such guide light unit 46 is a semiconductor laser providing a very low power, continuous laser beam. Unlike the Er:YAG laser, the semiconductor laser emits the beam in the visible region of the spectrum. The guide light beam is adopted to indicate the focal point of the operating laser beam as a visible light spot before the operating laser beam is applied. That is the operating beam is applied to the same area as the guide light beam spot. Therefore, an operator can start the operating laser after the guide light beam spot appears at the desired location. Thus, the continuous guide light laser beam serves aiming function simplifying targeting of the invisible pulse operating beam. In use, upon activation of the operating laser as well as the guide lasers, the continuous and the pulse beams are delivered to the targeted area. The operating laser can be easily focused at the targeted area based on the image of the guide light laser there. The disintegrated skin products accumulated at the site of the surgery are ultimately removed and disposed by the suction unit 16. In the embodiments of FIGS. 2 and 3 the suction unit is designed as a device independent from the handpiece and energized by the power supply unit 14 of the surgical device. Nevertheless, forming the suction unit as a part of the handpiece is also contemplated.

In the alternative embodiment the cooling arrangement can be positioned outside the handpiece. For instance, it can be associated with the power unit in such manner that a stream of cooling air is delivered to the interior of the handpiece through a flexible piping or similar arrangement.

In operation of the FIG. 2 embodiment, to excite the operating laser, high voltage is developed in the power supply unit 14 and applied across the flash lamp 28. In the laser cavity 22 the delivery of the light energy from the flash lamp is facilitated by the highly reflective interior surface thereof. The energy from the flash lamp 28 is absorbed by the medium of the laser rod 26, so that the molecules in the laser medium are transferred from the ground state to the excited state. As those molecules return to their ground state, they emit photons of a particular wavelength. Part of the light emanates from the laser rod. The light is returned to the rod by the mirrors 32 and 34. The returned photons react with molecules of the laser medium in the excited state to cause those molecules to return to the ground state and themselves emit photons of the particular frequency. Thus, the emitted photons are in phase with the photons striking the molecules and directed in the same direction as the original photons. In the operating laser the photons traveling between the mirrors 32 and 34 follow a specific paths, so that the photons resonate in particular modes at common frequency and phase. Eventually, the light between the mirrors 32 and 34 reaches such level of intensity that its substantial amount passes through the semi-reflective mirror 34 and is directed by the focusing lens 36 to the targeted area of the skin of a patient as an operating beam.

FIG. 3 illustrates the embodiment of the invention in which the laser surgical device is formed with two working cavities. An auxiliary cavity 17 is associated with the power supply unit 14. This cavity contains the exciting arrangement such as a flash lamp 28 and is connected through an activated fiber optic arrangement 19 to a main laser cavity 15. Similar to the embodiment of the FIG. 2, the main laser cavity 15 contains the active element or laser rod 26 and the optical resonator 30 having two mirrors 32 and 34. In operation, high voltage developed in the power supply unit 14 is applied to the exciting arrangement 28 of the auxiliary cavity 17 generating impulses of light energy. These impulses are delivered to the active element 26 situated in the main cavity 15 by means of the activated fiber optic arrangement 19.

In the embodiment of FIG. 3 the high voltage pulses energizing the flash lamp 28 are not transmitted directly to the handpiece. Instead, such high voltage pulses are delivered to the auxiliary cavity 17 situated remotely from the handpiece and an operator. This provides even higher degree of safety for the surgical device of the invention since chances of electrical shock hazards to the medical personal are effectively minimized.

Furthermore, since the exciting arrangement or the flash lamp 28 is positioned outside of the main cavity, the weight of the handpiece is greatly reduced simplifying manipulations of the device by a surgeon.

It is best illustrated in FIGS. 2 and 3 that during a surgery a condition of an operated tissue is monitored by a detecting arrangement or detector 48 adopted to detect irradiation reflected from that tissue. One of the main functions of the detector 48 is to control the effect of the operating laser beam on the skin of a patient in general and specifically to control the depth of penetration of the operating laser beam and the depth of vaporization of the epidermis. In every individual case a doctor sets specific characteristics of the laser irradiation to produce the required effect. If a predetermined depth of penetration of the operating laser beam and/or the thickness of the vaporized layer of a skin are achieved, the detector 48 generates a signal directed to the control unit 18 which in turn produces a correcting signal to the power unit or other units of the surgical device. Similar signals can be also produced when the prearranged levels of the energy density, power density or other characteristics of the operating laser are attained. This is necessary to exclude possibility of deeper penetration of the operating laser beam and/or damaging an adjacent healthy skin tissue. The intensity of the reflected light radiation from the skin of a patient depends upon such factors as: type and stage of a disease, color of a skin, general condition of a patient, the depth of a treated skin layer, etc. For each individual patient, considering the initial level of optical irradiation, such value of intensity characterizes a condition of an area of the skin treated by the laser surgical device of the invention. The detecting arrangement 48 can be made utilizing a wide variety of photoelements, photoresistors, photodiodes and similar devices. If a photoelement is used to form the detector 48, the light reflected from the targeted area of the skin produces a flow of electrons in the photoelement directed towards its cathode and generating an electrical current or a control signal forwarded to the control unit 18. In case photoresistors are utilized, the electrical resistance of the detector 48 varies depending upon the level of intensity of the light reflected from the operated tissue and received by the detector 48. The signal to the control unit 18 is based on such varying resistance.

Figure 4:
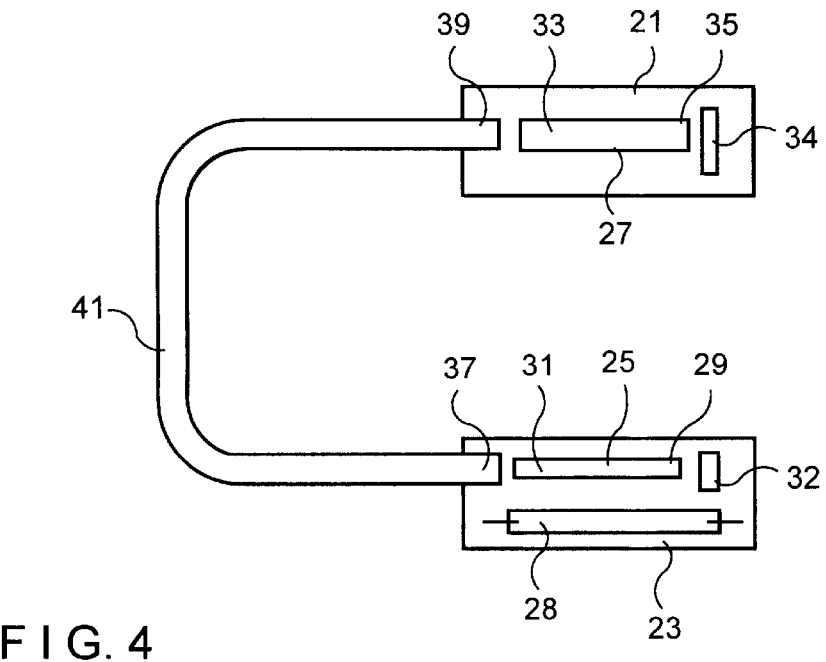
FIG. 4 shows a portion of a further embodiment of the laser surgical device.

In FIG. 4 schematically illustrates a part of the laser assembly of another embodiment of the invention in which only portions of the active element and optical resonator are positioned in the main working cavity 21 situated in the handpiece. To accommodate such arrangement an auxiliary cavity 23 is provided. The exciting arrangement 28 and a first or auxiliary part 25 of the active element are situated within the auxiliary laser cavity 23. A distal end 29 of the first part 25 of the active element faces the mirror 32 having high reflectivity, whereas a proximal end thereof 31 is positioned at an end 37 of the light guide 41. To facilitate efficient delivery of the light energy from the exciting arrangement 28 to the first portion 25 of the active element the interior of the auxiliary cavity can be formed from a material having high reflective properties. A second or working part 27 of the active element and a semi-reflective mirror 34 of the optical resonator are situated in the main working cavity 21. The distal end 33 of the second part 27 of the active element and the proximal end 31 of the first part thereof are optically connected through a fiber light guide 41. Both ends of the light guide situated in the vicinity of the active element can be manufactured as parts of the optical resonator. In this respect, the end 37 of the light guide positioned in the auxiliary cavity 23 can be formed as a mirror having characteristics facilitating passage of the laser irradiation from the first part 25 towards the second part 33 of the active element. To facilitate the required operating laser beam operation from the main cavity 21, the end 39 of the light guide situated thereinside can be formed as a mirror enabling passage of irradiation only in the direction of the second part 27 of the active element. As in the previously discussed embodiment of FIG. 3, an operator is provided with an instrument devoid of electrical shock hazard and having considerably reduced weight. This is an important advantage of the present invention especially during prolonged surgical operations.

Figure 5:
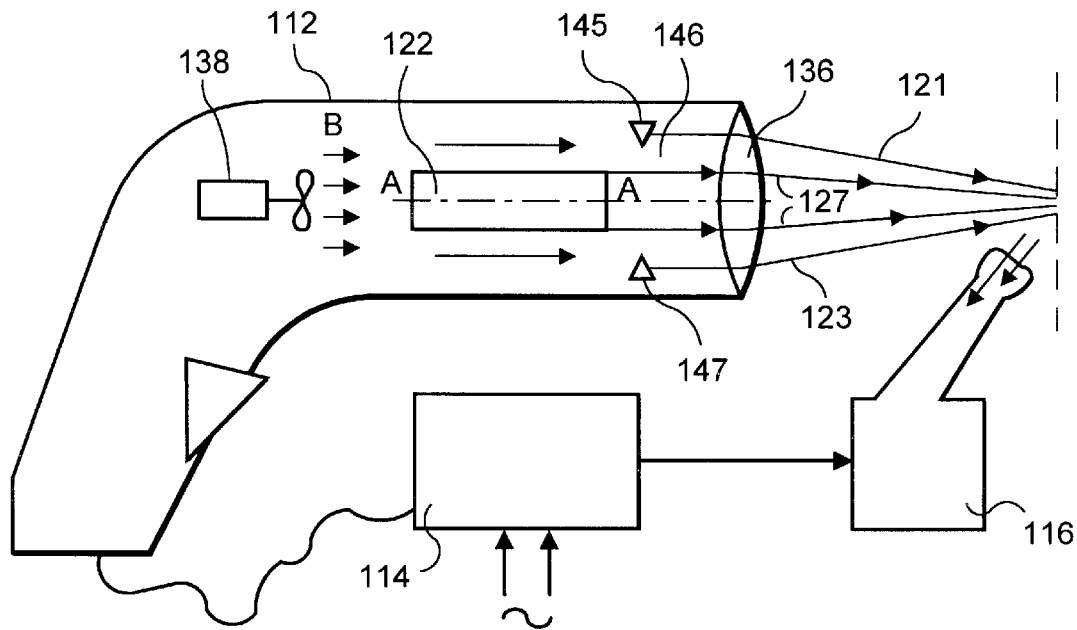
FIG. 5 shows a simplified embodiment of the laser surgical device.
Figure 6:
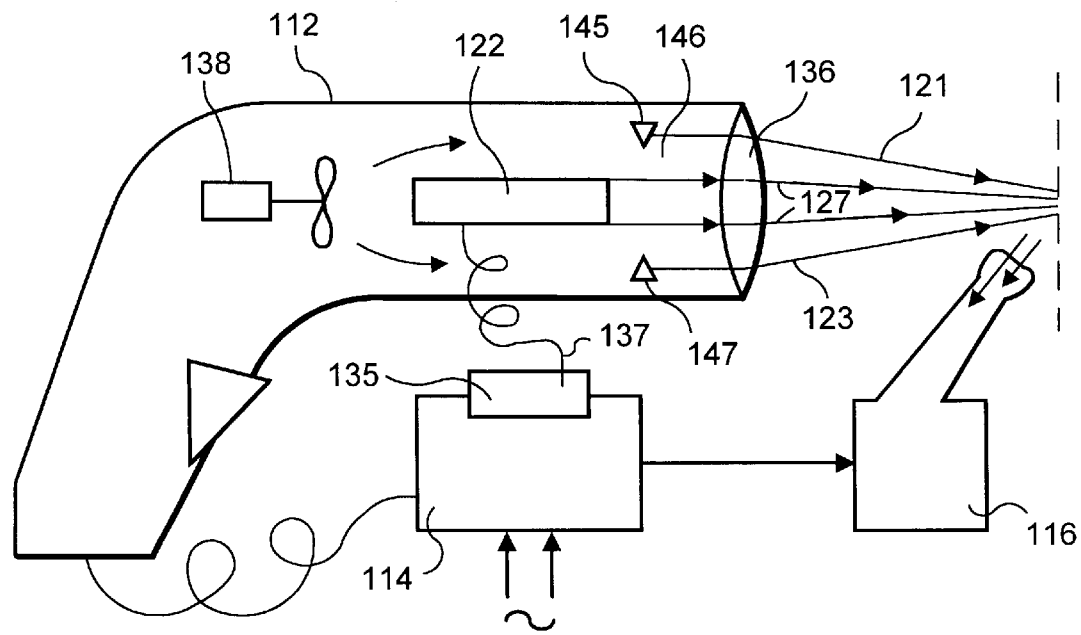
FIG. 6 shows another simplified embodiment of the laser surgical device.

A further simplified embodiment of the laser surgical device is best illustrated in FIGS. 5 and 6. It is shown in FIG. 5 that a handpiece 112 which resembles a housing of a hair drier contains an operating pulse laser 122, a cooling fan 138 and a light guide arrangement 146. In order to provide an axial air flow directed toward a patient, the fan 138 is positioned rearwardly of the operating laser. Two light-emitting diodes 145 and 147 of the light guide arrangement 146 are installed within the housing between the operating laser and the focusing lens 136. The light-emitting diodes are arranged in such a manner that the distance between the images of their light guide beams 121 and 123 in the focal plane of the focusing lens 136 is substantially equal to the diameter of the spot of the operating beam 127 of the operating Laser 122 in this plane. Therefore, the targeted area of the operating beam spot can be identified by watching the visible images of the light guide beams. The dimensions of this operating beam spot can be adjusted by changing the distance between such visible images. The power supply unit 114 energizes not only the laser, fan and light guide arrangement but also the suction unit 116 positioned outside the housing. For the safety reasons all power feeding cables can be jacketed by earthen metal hoses. The pulse rate and the pulse energy of the operating laser 122 are set manually by generating a command from the control panel of the power supply unit 114. Similar to previously described embodiments, the suction unit 116 provides removal of the fragments of the disintegrated particles of skin developed during the surgery. The focusing lens 136 can be made of a quartz glass.

The laser surgical device of FIG. 6 is similar to that of FIG. 5. However, in FIG. 6 the exciting arrangement 135 is positioned outside the handpiece 112 and the impulses of light energy are delivered to the operating laser 122 by means of a light guide 137. In this respect, the instrument of FIG. 6 operates in a manner similar to the embodiment of FIG. 3. The modified embodiment of FIG. 6 in which a portion of the active laser element or rod is situated outside of the handpiece (see FIG. 4) is also contemplated.

In the embodiments illustrated in FIGS. 5 and 6 the focusing lens 136 is moved manually a predetermined distance. During such movement the position of images generated by the light-emitting diodes 145 and 147, which determine the size of the operating laser spot in the focal plane, is automatically changed.

If the motion of the lens 136 is provided in the direction substantially perpendicular to the operating beam axis A—A, a series of laser beam images may be obtained in the focal plane. For example, FIG. 11 illustrates this condition for the normal and FIG. 12 for cylindrical lenses.

Upon motion of the focusing lens in the direction parallel to the axis of the beam it is possible to obtain a more complex image pattern, i.e. circular (see FIG. 13), spiral patterns (see FIG. 14).

Depending upon the type of operation, replacement of the focusing lens is possible in the present invention. Typically, the most suitable lens is one having an optical element smoothly traveling along the axis of the operating laser beam, so that the optical element can be fixed at a prearranged intermediate position. In this respect, FIG. 7 illustrates the focusing lens 137 having three such intermediate positions.

The size of the operating laser spot in the focusing region can be regulated by the micromotor upon a signal from the control unit 18 (see FIG. 2). This can be also accomplished manually by an operator or according to a prearranged program. Thus, the size of the operating laser spot of the operating laser beam can be adjusted in the focal plane of the focusing lens up to the sizes at which irregularities of the laser spot are still acceptable.

Figure 8:
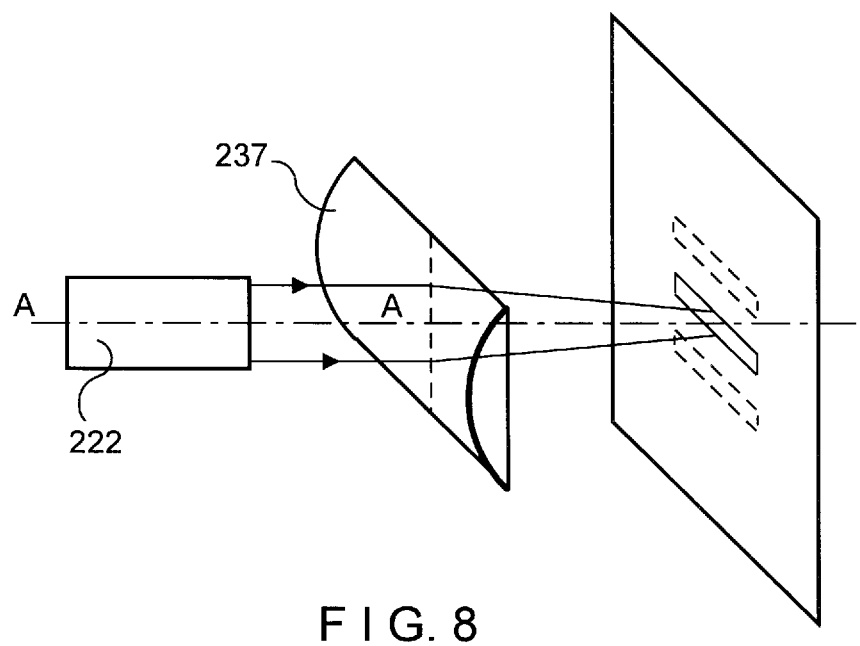
FIG. 8 shows a laser surgical device having substantially cylindrical focusing lens.

The focusing lens shown in FIG. 8 produces the operating beam in the form of an oblong strip. This is achieved by using a semi-cylindrical lens 237. The required changes in the form of this strip can be provided by rotating and guiding the lens 237 in a predetermined fashion.

Figure 9:
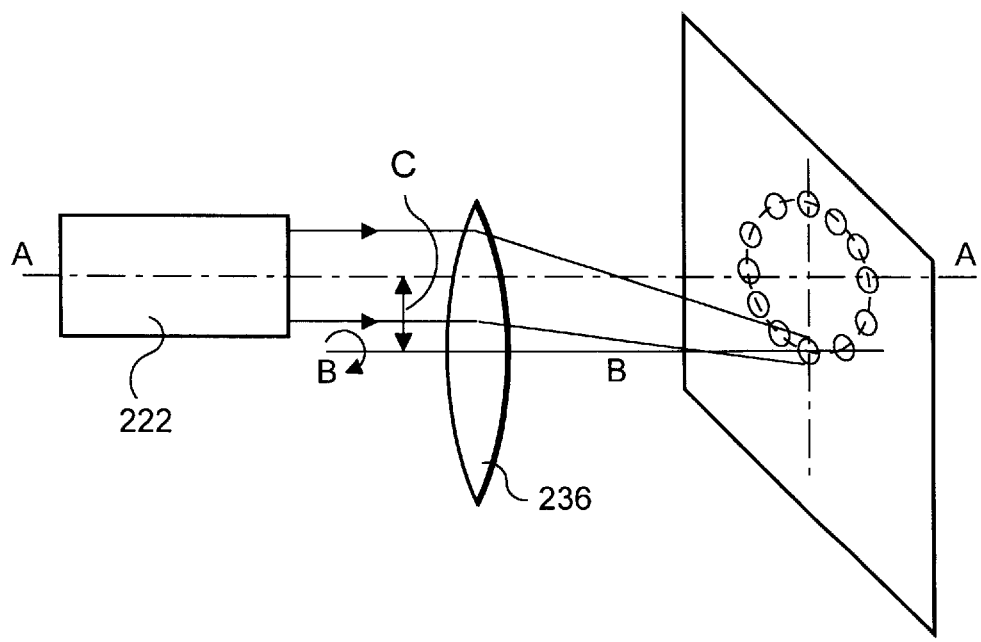
FIG. 9 shows a laser surgical device with the focusing lens movable about shifted axis.

The embodiment of the focusing lens 236 illustrated in FIG. 9 enables the invention to produce a trace of movement of the focused operating laser beam in the form of a ring. This is achieved by rotating the focusing lens 236 about its axis B—B which is shifted a predetermined distance C from the axis A—A of the operating laser beam.

As to the embodiment of FIG. 10, it illustrates a supplemental focusing lens for the precise focusing of the operating laser beam on the targeted area. For this purpose it is advisable initially to fixedly attach the laser assembly 222 with the lenses 236, 239 and the mirrors 245, 247 at the prearranged condition. The visible guide light should be prealigned with the invisible operating laser beam. In this case it desirable to keep stationary at least a part of the patients body which is the subject of a surgery. A special device can be provided to accomplish this task.

The surgical device of the invention utilizes laser irradiation within the entire spectrum of the wavelength corresponding to the "windows of non-transparency" of water. At the density of the laser irradiation of the operating beam spot 5–10 J/cm$^2$ and the diameter of the operating laser beam spot 3–10 mm, the depth of penetration of the operating laser beam of the invention into the epidermis does not exceed 10–20 microns. This occurs upon application of impulses having a very short duration of about 0.001 sec. After dehydration of the tissue, the spot of the operating laser beam produces only local vaporization of the top layer of the skin of a patient. This occurs without damaging in depth as well as superficially healthy regions of epidermis surrounding the operated area. The treated area of the tissue can be increased by moving the spot of the operating laser beam over the surface of the skin. The depth of penetration of the operating laser beam into the living tissue can be manipulated by changing the frequency of the electromagnetic impulses. Typically, during a session having duration of 30–60 seconds about 50–100 impulses are provided.

The laser surgical device of the invention can be also utilized for disinfecting lesions by scattered infrared laser emission. The density of this type of emission does not produce damage to normal healthy skin. However, such emission eliminates staphylococcal colonies in the skin area damaged by a disease.

The optical system of the laser surgical device also enables a user to perform surgical operations which are followed by the laser photocoagulation and laser dissection including ablation of cancerous tumors. The present invention also facilitates removal of a benign tumor by vaporization of one layer of tissue at a time. This task can be accomplished through application of several laser impulses having a predetermined spot area to each part of the skin affected by the decease. The treatment is continued until appearance of the "blood dew" symptom on the skin and typically followed by a drug treatment course.

To carry out a therapy of the skin by infrared radiation to remedy, for example, face wrinkles, the laser surgical device of the invention can be used in combination with a scanning system of a preset scattered radiation. In order to utilize this treatment it is expedient to secure conditions of the beam scanning according to a preset program (the spot diameter of the operating beam can vary in a predetermined fashion, the density of energy of the beam can be either variable or constant, see FIG. 15). The same condition can be provided if the laser beam is in a form of a slot (see FIG. 16).

The focused laser irradiation of the invention can be utilized for conducting of local surgeries, such as, for a example, dissection and removal of a furuncle or a pustule and consequent introduction of a medicine into the area of the incision.

The following examples are presented in order to provide more complete understanding of the invention. The specific techniques, conditions, materials and results set forth to illustrate the principles and practice of the invention are exemplary and should not be construed as limiting the scope of the invention.

EXAMPLE 1

Er:YAG laser was employed as an active element of the laser surgical device having a flash lamp as the exciting arrangement. The Er:YAG active element was interposed between two substantially flat resonator mirrors. The lasing occurred at the wavelength of 2.94 $\mu$m with the pulse duration 250±50 microseconds, the pulse rate up to 1 Hz and the pulse energy up to 2 J.

The shape of the operating laser beam was adjusted by the focusing arrangement. Since Er:YAG laser beam belongs to the infrared region of the spectrum it was invisible to the naked eye of the operator. The position and dimensions of the laser spot of the operating laser beam on the skin of a patient were indicated with help of two guide light beams generated by the guide semiconductor laser which emitted the beam in the visible region of the spectrum. The maximum diameter of each guide light laser beam was about 2.0 mm. The distance between projections of two guide light laser beams on the skin of a patient corresponded to the spot diameter of the Er:YAG laser on the same object. Thus, the position and diameter of the Er:YAG laser beam on the skin of the patient was determined by the position of two guide light laser beams emitted by the guide light semiconductor laser. The energy density of the Er:YAG laser was adjustable within the range between 1.0–10 J/cm$^2$. Considering that during the treatment the level of the pumping energy was about the same, the smaller was the dimension of the Er:YAG laser beam, the higher was its energy density. Upon reaching minimal focusing dimensions of the spot of Er:YAG laser beam on the skin of a patient a local vaporization of the tissue occurred at the depth up to 1.5 $\mu$m. Visible vaporization from the epidermis took place when the energy density of the Er:YAG laser beam was about 50 J/cm$^2$.

Treatment of skin diseases of 48 patients was carried out by using surface vaporization of epidermis by Er:YAG laser with 50 J/cm$^2$ maximum energy density. Among them 15 patients were with pointed condylomas, 8 patients with colloidal scars, 8 patients with warts on hands and feet, 10 patients with pointed hyporkeratosises, 7 patients with tattoos. Depending on the type of the disease or skin defect, the treatment was carried out by conducting 6–10 sessions, each consisting of 3–20 pulses.

During these sessions the diameter of the spot of the Er:YAG laser beam was 3–5 mm. The coagulation degree control was performed until appearance of the "blood due" symptom. As a result of such application of the laser beam to the skin of the patients there had been no changes detected in the peripheral blood content and no remote relapses of the disease revealed.

EXAMPLE 2

Unlike Example 1, there were two working cavities provided in the laser device of Example 2. In the first cavity electrical pulses were transformed into light pulses. Such light pumping pulses were received via the optical light guide in the second cavity. There the light pulses were transformed into the laser beam. The first cavity was situated at the power supply unit remotely from the patients and medical personnel. The second cavity was located within the handpiece of the surgical device. In this example another set of the working cavities was formed in such a manner that the first cavity contained the exciting arrangement and a portion of the operating laser rod, whereas the main part of the laser rod was situated in the second cavity. The cavities were also interconnected by the optical fiber light guide. The laser pulses received within the second cavity were of such pumping wavelength as to minimize losses in the optical light guide. The laser pulses generated in the second cavity were transformed into the laser irradiation beam operating of the required wavelength, for example, 2.94 $\mu$m.

We claim:

1. A laser device for conducting dermatological surgery, comprising:
    a housing having interior and exterior regions;
    a laser cavity extending within said interior region along a longitudinal axis of the housing, said laser cavity containing an operating laser element having at least an outer part and an exciting arrangement for exciting of said operating laser element, said operating laser element generating an operating beam;
    a cooling arrangement, said cooling arrangement forming a stream of gaseous coolant within the interior region of the housing, said stream of gaseous coolant being directed along a longitudinal axis of the laser element;
    said laser cavity and said operating laser element being situated entirely within said stream of gaseous coolant; and
    said housing forming a part of a handpiece adapted for convenient positioning in a hand of an operator and at least a portion of said cooling arrangement is situated within an interior portion of said handpiece.

2. The device of claim 1, further comprising a detecting arrangement for detecting a condition of an operated living tissue by receiving and reviewing a signal reflected from said operated living tissue and producing a control signal; and a control unit for controlling and adjusting characteristics of said operating beam in response to said control signal.

3. The device of claim 2, wherein said detecting arrangement is selected from the group consisting of photoelements, photoresistors and photodiodes; and said guide light unit provides a continuous low power beam and is selected from the group consisting of a filament lamp; He:Ne laser, a semiconductor laser and light emitting diodes.

4. The device of claim 1, further comprising a focusing arrangement for focusing said operating beam at an operated living tissue and a guide light unit generating a guide light beam for targeting of said operating beam at said operated living tissue.

5. The device of claim 4, further comprising a suction arrangement for removal of disintegrated tissue products produced during the surgery from an area of said operated living tissue.

6. The device of claim 4, wherein at least a portion of said guide light unit is situated within an interior portion of said handpiece.

7. The device of claim 6, wherein said cooling arrangement is a fan producing said stream of gaseous coolant.

8. The device of claim 6, wherein said operating laser element consists of working and auxiliary parts, said working part is situated within said handpiece, said auxiliary part is situated outside of said handpiece, said working and auxiliary parts of the operating laser element are connected through a light guide consisting of at least one fiber.

9. The device of claim 8, wherein said exciting arrangement consists of working and auxiliary parts, said working part is situated within said handpiece and said auxiliary part of the exciting arrangement situated outside of said handpiece, said working and auxiliary parts of the exciting arrangement are connected by a light guide consisting of at least one fiber.

10. The device of claim 4, wherein said laser cavity, said cooling arrangement, said focusing arrangement and said guide light unit are situated within said interior portion of the housing in such a manner that relative to the direction of said stream of gaseous coolant at least a part of said cooling arrangement is positioned rearwardly of said laser cavity and said guide light unit is situated forwardly of said laser cavity facing said focusing arrangement.

11. The device of claim 1, wherein said operating laser element generates an operating beam with wavelength between 2.9 and 3.0 microns.

12. The device of claim 1, wherein said operating laser element is Er:YAG laser rod.

13. The device of claim 1, wherein said operating laser element generates an operating beam with wavelength operating beam selected from the group consisting of the following ranges: 1.25–1.40; 1.7–2.1; 2.5–3.1 and 5.5–7.5 microns.

14. The device of claim 1, wherein a laser medium of said operating laser element is selected from the group consisting of $Y_3AL_5O_{12}$:Nd; $Gd_3Ga_5O_{12}$:Cr, Ce, Nd; $MgF_2$:Co; $BaYb_2F_8$:Er; $LiYF_4$:Er, Tm, Ho; $Y_3Sc_2Al_3O_{12}$:Cr, Er; $(Y, Er)_3Al_5O_{12}$; HF (chemical) and CO (gaseous).

15. The device of claim 1, wherein said exciting arrangement is selected from the group consisting of a flash lamp and a diode laser.

16. A dermatological laser surgical device, comprising:
a housing having interior and exterior regions;
a laser cavity extending within said interior region, said laser cavity containing an operating laser element having at least an outer part and an exciting arrangement for exciting of said operating laser element, said operating laser element generating an operating beam;
a cooling arrangement, said cooling arrangement forming a stream of gaseous coolant within the interior region of the housing, said stream of gaseous coolant being directed along a longitudinal axis of the operating laser element;
said operating laser element being situated entirely within said stream of gaseous coolant;
a detecting arrangement for detecting conditions of an operated living tissue by receiving and reviewing signals reflected from said operated living tissue and generating a control signal; and
said housing forming a part of a handpiece adapted for convenient positioning in a hand of an operator and at least a portion of said cooling arrangement is situated within an interior part of said handpiece.

17. The device of claim 16, further comprising a control unit for controlling and adjusting characteristics of said operating beam in response to said control signal, a focusing arrangement for focusing said operating beam at an operated living tissue, and a guide light unit generating a guide light beam for targeting of said operating beam at said operated living tissue.

18. The device of claim 17, wherein at least a portion of said guide light unit is situated within an interior portion of said handpiece.

19. The device of claim 18, wherein said cooling arrangement is a fan producing said stream of gaseous coolant within said interior portion of said handpiece.

20. The device of claim 18, wherein said operating laser element consists of working and auxiliary parts, said working part is situated within said handpiece, said auxiliary part is situated outside said handpiece, said working and auxiliary parts of the operating laser element are connected through a light guide consisting of at least one fiber.

21. The device of claim 18, wherein said exciting arrangement consists of working and auxiliary parts, said working part is situated within said handpiece and said auxiliary part of the exciting arrangement situated outside of said handpiece, said working and auxiliary parts of the exciting arrangement are connected by a light guide consisting of at least one fiber.

22. A laser device for conducting dermatological surgery comprising:
a housing having interior and exterior regions;
a laser cavity extending within said interior region along a longitudinal axis of the housing, said laser cavity containing an operating laser element having at least an outer part and an exciting arrangement for exciting of said operating laser element, said operating laser element generating an operating beam;
a cooling arrangement, said cooling arrangement forming a stream of gaseous coolant within the interior region of the housing, said stream of gaseous coolant being directed along a longitudinal axis of the laser element;
said laser cavity and said operating laser element being situated entirely within said stream of gaseous coolant;
a guide light unit generating a guide light beam for targeting said operating beam at said operated living tissue; and
said housing forming a part of a handpiece adapted for convenient positioning in a hand of an operator, so that at least portions of said cooling arrangement and said guide light unit are situated within an interior part of said handpiece.

* * * * *